United States Patent
Luck et al.

(10) Patent No.: US 6,217,932 B1
(45) Date of Patent: Apr. 17, 2001

(54) METHOD OF OBTAINING HAEMIN FROM SLAUGHTER BLOOD

(75) Inventors: Thomas Luck, München; Andreas Mäurer, Freising, both of (DE)

(73) Assignee: Fraunhofer-Gesell schaft zur Forderung der Angewandten Forschung E.V., Munich (DE)

(*) Notice: Subject to any disclaimer, the term of this patent is extended or adjusted under 35 U.S.C. 154(b) by 0 days.

(21) Appl. No.: 09/331,373
(22) PCT Filed: Nov. 21, 1997
(86) PCT No.: PCT/DE97/02748
   § 371 Date: Aug. 11, 1999
   § 102(e) Date: Aug. 11, 1999
(87) PCT Pub. No.: WO98/28302
   PCT Pub. Date: Jul. 2, 1998

(30) Foreign Application Priority Data

Dec. 20, 1996 (DE) ................................. 196 53 482
Sep. 30, 1997 (DE) ................................. 197 43 330

(51) Int. Cl.⁷ .................. A23J 1/06; A23K 1/04
(52) U.S. Cl. .............. 426/647; 426/74; 426/478; 426/520
(58) Field of Search .............. 426/74, 647, 520, 426/478; 424/439

(56) References Cited

U.S. PATENT DOCUMENTS

| 4,376,727 | * | 3/1983 | Sato et al. ................... 426/647 |
| 4,431,581 | * | 2/1984 | Lindroos ..................... 426/647 |
| 4,761,472 |   | 8/1988 | Schultze . |
| 5,872,227 | * | 2/1999 | Erlansson et al. .............. 426/647 |

FOREIGN PATENT DOCUMENTS

| 36 08 091 |   | 9/1987 | (DE) . |
| 1063247   | * | 4/1986 | (JP) ........................... 426/647 |
| 405523    | * | 8/1971 | (SU) .......................... 426/647 |

OTHER PUBLICATIONS

Schumann et al., Intestinal Transfer of Different Haemin Preparations in Vitro.: Ital. J. Gastroenterol., 27: 167 (1995).

* cited by examiner

Primary Examiner—Helen Pratt
(74) Attorney, Agent, or Firm—Barnes & Thornburg

(57) ABSTRACT

The invention concerns a method of obtaining haemin. In order to separate haemin from the globin part, slaughter blood is subjected to an acid treatment at a pH of between 1.2 and 3 and a temperature of between 45 and 80° C., the haemin then being separated from globin.

13 Claims, 1 Drawing Sheet

METHOD OF OBTAINING HAEMIN FROM SLAUGHTER BLOOD

CROSS-REFERENCES TO RELATED APPLICATIONS

This application is a U.S. national application of international application serial No. PCT/DE97/02748 filed Nov. 21, 1997, now WO 98/28302 which claims priority to German Serial Nos. 196 53 482.8 and 197 43 330.8 filed Dec. 20, 1996 and Sep. 30, 1997, respectively.

BACKGROUND AND SUMMARY OF THE INVENTION

It is known from the literature (e.g. Allgemeine und spezielle Pharmakologie und Toxikologie ["General and special Pharmacology and Toxicology"], edited by W. Forth, D. Henschler et al., 5th edition, B1 Wissenschaftsverlag, Mannheim, 1987, page 389 ff.) that heme iron is suitable for the fortification of various materials by iron. In contrast to the iron that is contained in food, the advantage of heme iron can be seen in the feature that the iron in food is present predominantly as non-heme iron, whose availability is reduced by plant-based nutritive ligands (phytates, oxalates, tannin, etc.). Heme iron is not subject to these resorption restrictions and, moreover, it irritates the intestinal mucous membrane considerably less in high doses and it is tolerated better as a result.

However, no processes have become known so far from the literature by means of which hemin preparations can be manufactured with a correspondingly high concentration of globin. It has merely become known from the article by K. Schümann and A. Mäurer et al. in Ital. J. Gastroenterol. 27, 167, 1995, namely "Intestinal transfer of different hemin preparations in vitro", that heme iron is suitable for fortification by means of iron and that it can be prepared by acid hydrolysis.

Proceeding on the basis of this, the problem for the present invention is to propose a process for obtaining heme iron which is suitable for fortification by means of iron, whereby the hemin preparation that has been manufactured is required to contain a high concentration of globin (protein).

The problem is solved by the characterizing features of patent claim 1. The subsidiary claims indicate further advantageous embodiments.

DETAILED DESCRIPTION OF THE INVENTION

Figure 1:
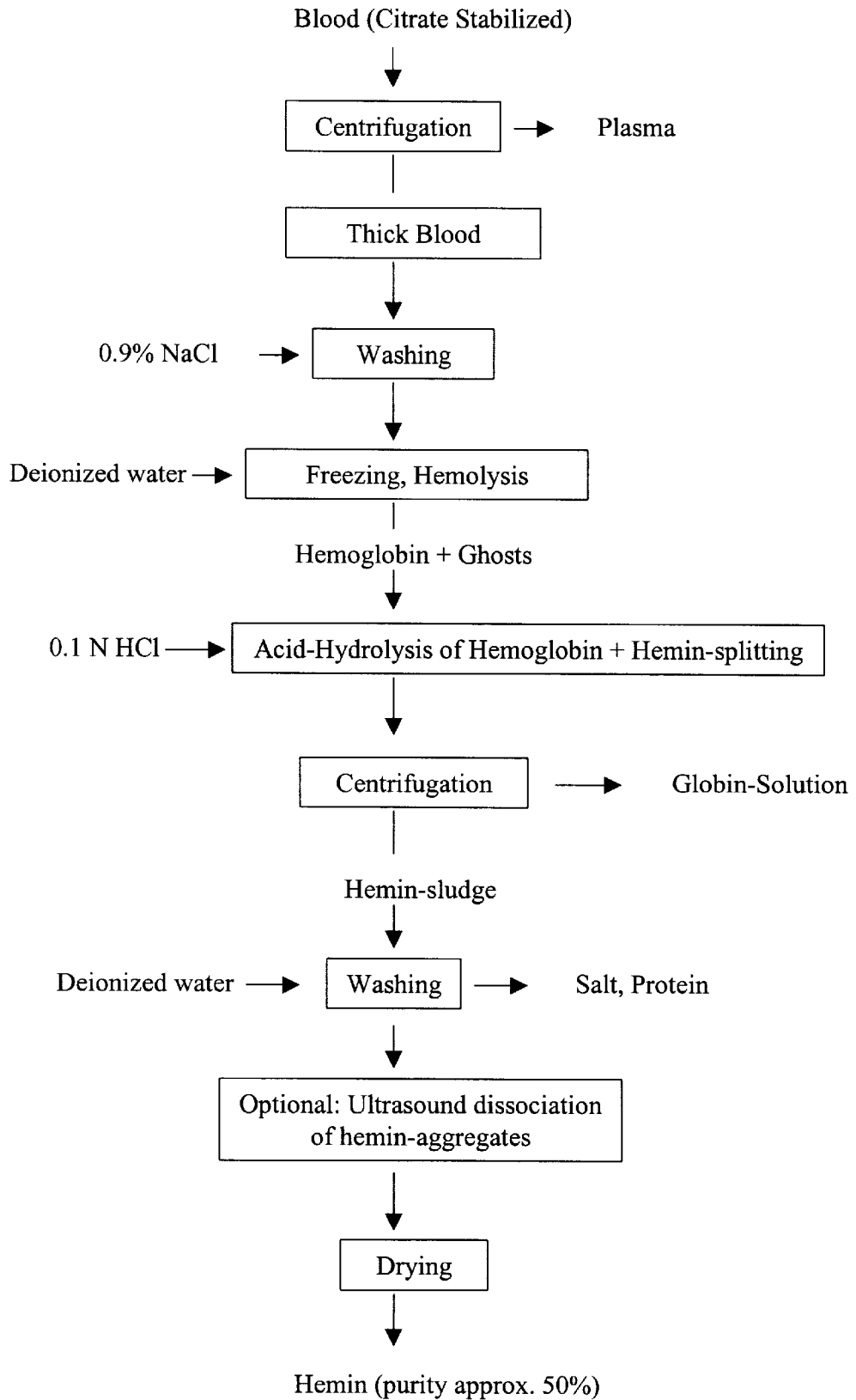
FIG. 1 is a diagram of the procedure for separating hemin from globin in accordance with the present invention.

Thus, in accordance with the invention, it is proposed that an acid treatment be carried out under exactly defined conditions starting from slaughter house blood. In accordance with the invention, it is proposed that slaughter house blood be subjected to an acid treatment at pH 1.2 to 3 at 45 to 80° C. in order to separate the hemin from the globin portion. It has been found that an appropriate hemin preparation is obtained only under these exactly defined conditions.

During the process in accordance with the invention, it is preferred in this connection that the separation of the slaughter house blood into a thick blood fraction and a plasma fraction be carried out prior to the acid treatment and that the acid treatment then be carried out only on the thick blood fraction.

It is especially preferred that the acid treatment takes place at a pH of 1.3 to 2.0 and at a temperature of 60 to 75° C. It is also preferred in the process in accordance with the invention that the hemin is first separated from the globin after a defined agglomeration time, preferably after a time of 15 minutes to 2 hours or, especially preferably, after 30 minutes to 1.5 hours. It has also been found that it is advantageous to work with relatively dilute solutions (at a preferred concentration range up to 10%) and extended aggregation times (up to 1 hour) in order to maximize the hemin content of the preparation. The ability to separate the hemin and the yield per precipitation-based preparation are increased simultaneously as a result of this, so that improved product quality arises with no throughput loss. The following were established as the optimal parameters for acid cleavage and loss. The following were established as the optimal parameters for acid cleavage and subsequent polymerization of the hemin: hemin/globin concentration: 3.5%; pH value: 1.5; temperature: 72° C. and reaction time: 50 minutes.

In order to improve the good bio-availability still further, an additional process valiant provides for the dissociation of the hemin aggregates by means of ultrasound prior to drying the hemin, whereby this drying process has to be carried out after the last step in the process in each case. For this purpose, the moist hemin product can be treated for 5 to 60 minutes or, preferably, for 15 minutes in an ultrasonic bath and then dried in a freeze drier.

The advantage of the process in accordance with the invention comprises the features in particular, that it is possible to utilize the cost-generating waste slaughter house blood product to give a decolorized globin fraction and an iron-containing hemin product. The hemin product, that is manufactured with the process in accordance with the invention, also has high iron bio-availability and opens up the following usage possibilities:

additive for the fortification, by means of iron, of plant-based food for humans (foodstuff additive, especially for a third world diet) and animal feed (e.g. for fattening pigs);

pharmaceutical iron preparations which are tolerated well.

The process in accordance with the invention also has the advantage that, as a result of the selected process conditions, effective inactivation takes place or pathogenic bacteria/germs and viruses that are possibly present in the slaughter house blood. In addition, degrading enzymes, which reduce product quality (proteases etc.), are inactivated. Because of the intact natural binding of the iron in the hemin (complexation via the protoporphyrin ring), the strong catalytic potential of the iron in terms of the oxidation of fatty acids and the degradation of amino acids if found to give no cause for concern.

The invention will be elucidated in more detail below on the basis of FIG. 1 and several examples of embodiments. FIG. 1 shows, by way of an example, the course of the process for obtaining hemin with a purity of >50% in the case where separation into the thick blood fraction and the plasma fraction takes place before the acid treatment.

As can be seen from FIG. 1, the blood, which is advantageously stabilized with citrate, is centrifuged and the plasma fraction is then separated from the thick blood fraction. The thick blood fraction is then frozen after a washing step with sodium chloride solution.

In order to carry out acid hydrolysis, the thick blood fraction, which has been prepared in this way, is mixed with 0.1 normal HC1 so that precipitation of the hemin takes place. Centrifugation is carried out in order to separate the globin solution from the heme sludge. The heme sludge is then washed with demineralized water and subjected to ultrasonic treatment, if required. Finally, drying takes place.

PREPARATION EXAMPLE

1. Small Scale Laboratory Preparation 50 ml of blood are centrifuged for 15 minutes at 3,300 g. 12 ml of the thick blood fraction (erythrocytes) and 38 ml of colorless blood plasma are formed. The erythrocytes are subsequently washed twice with, in each case, 40 ml of 0.9% NaCl solution and then centrifuged. The thick blood fraction (20 g), that has been washed, is made up to volume with 30 g of deionized water and shock frozen at −70° C. After 3 hours, it is thawed out at room temperature; the erythrocyte membranes (ghosts) are centrifuged off and the supernatant liquor, i.c, the hemoglobin solution, is transferred to a 250 ml Erlenmeyer flask. The deep red solution is adjusted to pH 1.5 with 1 normal HCl using a magnetic stirrer with a hot plate: after reaching 71° C., gentle stirring (150 rpm) is maintained at this temperature for 30 minutes. A sediment, i.e. the heme sludge is formed after cooling without stirring and this is centrifuged off for 15 minutes in the centrifuge at 3,300 g. Subsequently triple washing with 0.1 normal HCl and renewed centrifugation gives the hemin product with a hemin content of approximately 40% and a yield of 70%.

In order to improve its good bio-availability still further, dissociation of the hemin aggregates by means of ultrasound optionally takes place prior to drying the hemin. For this purpose, the moist hemin product is treated for 15 minutes in an ultrasonic bath and then dried in the freeze drier.

2. Large Scale Laboratory Preparation 8 l of deionized water are heated to 67° C. in a 15 l stirred reactor with a steam-heated double jacket and then adjusted to pH 1.4 with approximately 1.5 l of 1 normal HCl and mixed with a 2 kg deep frozen (block) of the thick blood fraction. The temperature is maintained at 67° C.; the pH is adjusted to 2 and stirring takes place for 1 hour at 250 revolutions per minute. After switching off the stirrer, the heme sludge is separated using a plate separator (Westfalia TA1) at 9,000–10,000 rpm with a throughput rate of 0.2 l/minute. The moist product (dry substance content: 10%) is dried in a freeze drier without subsequent washing or, alternatively, in a circulating air belt drier with an air inlet temperature of 80° C. (purity: 30% hemin content; yield: 55% of theory).

0.06% hemin and 3.4% partially lysed protein are contained in the separated globin solution. Based on the separated quantity, this means, on the one hand, a hemin loss of 45%; on the other hand, it shows that good subsequent hemin purification (globin separation) is possible via subsequent washing.

Preparation of Derivatives

Analogous preparations are carried out in a 5 l glass beaker using a magnetic stirrer with a hot plate with, on each occasion, 500 g of frozen heme sludge and 2 l of ascorbic acid or 2 l of citric acid or 2 l of acetic acid. The reaction temperature amounts to 70° C.; the pH value is adjusted to 2,3 (for the ascorbate and citrate preparations) or to 1.7 (acetic acid). No significant differences were found in regard to yield, hemin content and bio-availability.

3. Preparation on the Pilot Plant Scale 10 kg of a deep frozen thick blood fraction in the form of a block (hemoglobin content: approximately 35%) are introduced into 90 kg of preheated 0.01 n HCl (75° C.) in a 150 l stirred container with direct steam heating and gentle stirring (150 rpm). The pH value is held constant at 1.6 via the automatic addition of 6 n hydrochloric acid. Hemolysis, acid cleavage of the hemin/globin bond, hemin aggregation and sedimentation of the heme sludge then take place. After a reaction time of 1 hour at 70° C., the suspension is separated by means of a decanter and the moist heme sludge (dry substance content: 12%) is dried via a belt drier at an air inlet temperature of 80° C. The product that has been prepared contains approximately 40% hemin (yield: 65% of theory).

Hemin preparations on the 1,000 liter scale take place in a 3,000 liter stirred container which is indirectly heated by steam. The experimental parameters correspond to the preparation above. The quantities used are 10 times greater.

100 kg of a deep frozen thick blood fraction in the form of a block (hemoglobin content: approximately 35%) are introduced into 900 kg of preheated 0.01 n HCl (75° C.) in a 3,000 l stirred container with indirect steam heating and gentle stirring (150 rpm). The pH value is held constant at 1.6 via the automatic addition of 6 n hydrochloric acid. Hemolysis, acid cleavage of the hemin/globin bond, hemin aggregation and sedimentation of the heme sludge then take place. After a reaction time of 1 hour at 70° C., the suspension is separated by means of a decanter and the moist heme sludge (dry substance content: 12%) is dried via a belt drier at an air inlet temperature of 80° C. The product that has been prepared contains approximately 40% hemin (yield: 65% of theory).

It is also meaningful to convert the discontinuous precipitation step into a continuous process for the large scale industrial preparation of hemin. In this way, energy, raw materials and waste water costs can also be reduced with circulatory operation using hot acidic globin solution. For this purpose, the addition and mixing of the dilute acid with the thick blood fraction takes place in a separate apparatus (stirred container) and the subsequent polymerization of the hemin and precipitation take place in a tubular or multitubular reactor in which a slow flow rate is produced with residence times of approximately 1 hour.

The protein is removed, via ultrafiltration, from the globin solution, which was separated by means of the decanter, and the permeate is used again for precipitating hemin.

A temperature of 75° C. over approximately 10 minutes was found to be the critical denaturing temperature for the process conditions in question. Acidic cleavage of thermally denatured hemoglobin is not possible.

What is claimed is:

1. A process for obtaining hemin from slaughter house blood comprising separating the slaughter house blood into a thick blood fraction and a plasma fraction; subjecting at least a portion of the thick blood fraction of the slaughter house blood to acid treatment at pH 1.2–3 at 45–80° C. to cleave in solution hemin from globin and to promote precipitation of hemin; and then separating the hemin in the precipitate from the globin in the hot acidic solution.

2. The process of claim 1 wherein the acid treatment is carried out at pH 1.3–2.0 at a temperature of 60–75° C.

3. The process of claim 2 wherein the hemin is separated from the hot acidic globin solution after an agglomeration time of 15 minutes to 2 hours.

4. The process of claim 3 wherein an agglomeration time of 30 minutes to 1.5 hours is maintained.

5. The process of claim 2 wherein a hemoglobin concentration of 2 to 10% is set up for the acid treatment.

6. The process of claim 1 wherein the hemin is separated from the hot acidic globin solution after an agglomeration time of 15 minutes to 2 hours.

7. The process of claim 6 wherein an agglomeration time of 30 minutes to 1.5 hours is maintained.

8. The process of claim 1 wherein a hemoglobin concentration of 2 to 10% is set up for the acid treatment.

9. The process of claim 1 wherein the heme is subjected to ultrasonic treatment prior to drying.

10. The process of claim 1 operated continuously.

11. The process of claim 1 wherein the hot acidic globin solution is purified from globin and the hot acidic solution is sent on to a circulatory operating system.

12. The process of claim 1 wherein the separation of hemin from globin is about 20 to about 80% complete.

13. The process of claim 1 further including fortifying foodstuff with the separated hemin.

\* \* \* \* \*